United States Patent [19]
Shimizu et al.

[11] Patent Number: 4,822,934
[45] Date of Patent: Apr. 18, 1989

[54] 1-(3-VINYLPHENYL)-1-PHENYLHYDROCARBONS AND METHOD FOR PRODUCING THE SAME

[75] Inventors: Isoo Shimizu; Yasuo Matsumura, both of Yokohama; Yutaka Arai, Tokyo, all of Japan

[73] Assignee: Nippon Petrochemicals Company, Limited, Japan

[21] Appl. No.: 165,727

[22] Filed: Mar. 9, 1988

[30] Foreign Application Priority Data

Mar. 12, 1987 [JP] Japan ................................. 62-57099

[51] Int. Cl.$^4$ ............................................. C07C 15/16
[52] U.S. Cl. ................................................... 585/25
[58] Field of Search ........................................ 585/25

[56] References Cited

U.S. PATENT DOCUMENTS 4,618,914 10/1986 Sato et al. .................... 585/25 X
4,761,508 8/1988 Shimizu et al. .................. 585/469

OTHER PUBLICATIONS

Kluiber, R. W., "Equilibrium of Para-Substituted Styrenes to Produce P-Xylenes", *Journal of Organic Chemistry*, 30(6), pp. 2037–2041 (1965).

*Primary Examiner*—Patrick P. Garvin
*Assistant Examiner*—George R. Fourson
*Attorney, Agent, or Firm*—Scully, Scott, Murphy & Presser

[57] ABSTRACT 1-(3-Vinylphenyl)-1-phenylhydrocarbons and method for producing the same. The invention further relates to 1-(3-vinylphenyl)-1-phenylethane which is used for preparing the former compound. The 1-(3-vinylphenyl)-1-phenylethylene is used as a new intermediate for preparing α-(3-benzoylphenyl)propionic acid (tradename: ketoprofen) through α-3-(1-phenylethenyl)phenyl)propionic acid or its alkyl ester. The ketroprofen is a useful medicine for the relief of pain and inflammation.

2 Claims, No Drawings

1-(3-VINYLPHENYL)-1-PHENYLHYDROCARBONS AND METHOD FOR PRODUCING THE SAME

BACKGROUND OF THE INVENTION (1) Field of the Invention

This invention relates to 1-(3-vinylphenyl)-1-phenylhydrocarbons and method for producing the same. More particularly, the invention relates to 1-(3-vinylphenyl)-1-phenylethylene and a method for efficiently producing the same, and further relates to 1-(3-vinylphenyl)-1-phenylethane which is used for preparing the former compound.

The 1-(3-vinylphenyl)-1-phenylethylene which is a new compound proposed in the present invention is used as an intermediate for economically preparing α-(3-benzoylphenyl)propionic acid (tradename: ketoprofen) represented by the following formula (IV) through α-(3-(1-phenylethenyl)phenyl)propionic acid or its alkyl ester which is represented by the following formula (III). The ketoprofen is a useful medicine for the relief of pain and inflammation.

Furthermore, the 1-(3-vinylphenyl)-1-phenylethylene can be efficiently prepared by dehydrogenating another new compound of 1-(3-vinylphenyl)-1-phenylethane.

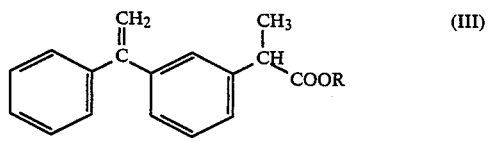

wherein R is a hydrogen atom or an alkyl group having 1 to 4 carbon atoms.

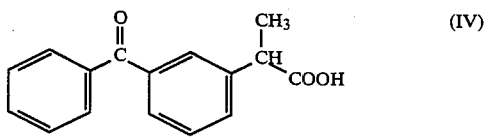

(2) Description of the Prior Art

There are proposed various methods for producing ketoprofen. Among them, typical methods are described in the following.

(1) 3-Benzoylpropiophenone is reacted with orthomethyl formate in the presence of thallium nitrate to produce the methyl ester of ketoprofen (British Pat. No. 2,019,393).

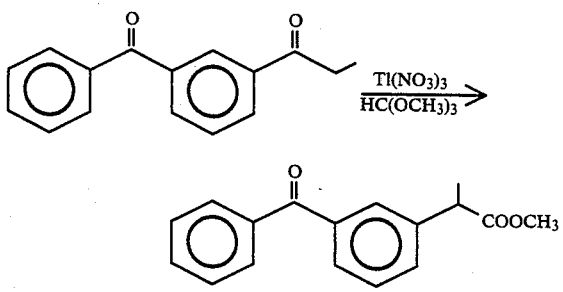

(2) 3-Benzylacetophenone is reacted with ethyl chloroacetate in the presence of a strong base to produce glycidic acid ester. This compound is then treated with an aqueous solution of sodium hydroxide to obtain a hydrolyzed and decarboxylated product of α-(3-benzylphenyl)propionaldehyde and it is further oxidized with potassium permanganate to obtain the ketoprofen (Japanese Laid-Open Patent Publication No. 55-36450).

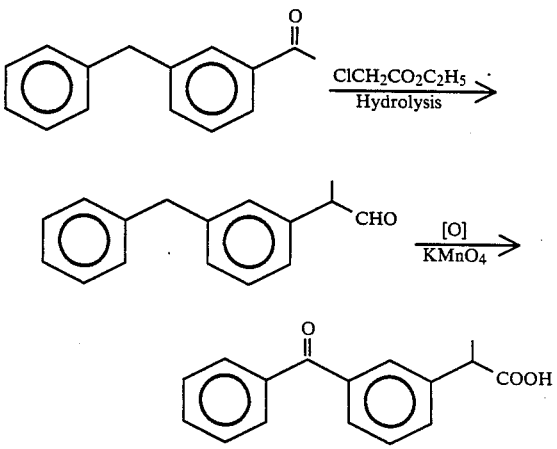

With regard to the method (1), even though the reaction process is short, it cannot be said that the synthesis of the raw material is easy and safe because the toxic thallium compound is used. Furthermore, it cannot be said that the starting material used in the method (2) is easily available. Accordingly, these methods (1) and (2) are not satisfactory in view of industrial production.

BRIEF SUMMARY OF THE INVENTION

It is, therefore, the primary object of the present invention to provide the intermediate compound for preparing ketoprefen (formula IV) at low cost and in a high yield.

Another object of the present invention is to provide 1-(3-vinylphenyl)-1-phenylethylene and a method for efficiently producing the same.

Still a further object of the invention is to provide 1-(3-vinylphenyl)-1-phenylethane which is used for preparing efficiently the above compound.

According to the present invention, the foregoing 1-(3-vinylphenyl)-1-phenylhydrocarbons are represented by the following formula:

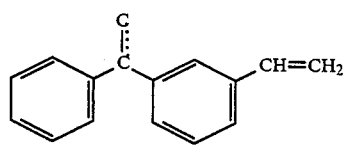

wherein represents a carbon-carbon double bond or a carbon-carbon single bond. More particularly, the compounds represented by the above formula is any one of the following formulae (I) and (II).

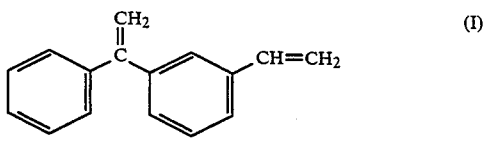

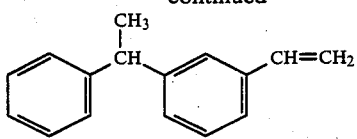

The specific feature of the present compound, 1-(3-vinylphenyl)-1-phenylethylene, are as follows.

(1) Hydroesterification is generally a carbonylation, that is, a insertion reaction of carbonyl group into an ethylenic double bond. The only vinyl group is, however, carbonylated by the hydroesterification of that compound under mild condition notwithstanding that compound has two ethylenic double bonds.

(2) The remaining double bond, that is, ethylidene group is easily oxidized with accompanying the decomposition of that bond to a carbonyl group.

(3) Therefore, ketoprofen, is produced easily, economically and in high purity from the present compound, 1-(3-vinylphenyl)-1-phenylethylene.

The compound of the formula (I), 1-(3-vinylphenyl)-1-phenylethylene can be synthesized without difficulty by the following exemplary process.

A method to use acetophenone (formula VIII) as a starting material is described. Acetophenone is reacted with a Grignard reagent of 3-vinylphenylmagnesium bromide (formula VII) to obtain 1-(3-vinylphenyl)-1-phenylethyl alcohol (formula V) (hereinafter referred to as "VPA"). The reaction product is then dehydrated in the presence of potassium hydrogensulfate to form 1-(3-vinylphenyl)-1-phenylethylene (formula I). This Grignard addition reaction is carried out at a temperature in the range of 0° to 100° C., preferably 20° to 80° C. The dehydration is carried out at 170° to 250° C., preferably 190° to 230° C., under a reduced pressure. The quantity of Grignard reagent is 1.0 to 1.2 equivalents relative to the acetophenone.

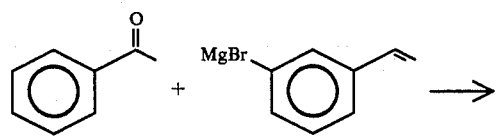

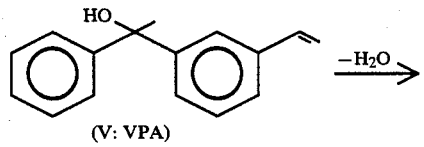

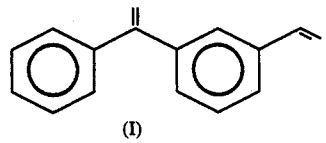

Besides the above process, the 1-(3-vinylphenyl)-1-phenylethylene of the formula (I) can be efficiently prepared without difficulty by dehydrogenating the new compound of the present invention of 1-(3-vinylphenyl)-1-phenylethane of the formula (II).

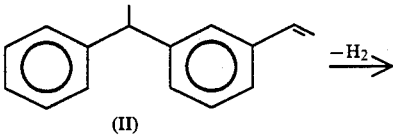

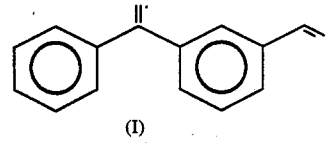

The 1-(3-vinylphenyl)-1-phenylethane of the formula (II) can be prepared at a high yield by, for example, the following process.

(1-Chloroethyl)benzene (formula VI) is subjected to coupling reaction with a Grignard reagent of 3-vinylphenylmagnesium bromide (formula VII) in the presence of a catalyst of nickel chloride (II)-diphosphine complex, to obtain 1-(3-vinylphenyl)-1-phenylethane. The reaction is carried out in a nitrogen atmosphere under atmospheric pressure at a temperature of 0° to 80° C. The ratio of (VI)/(VII) may be in the range of about 1.0 to 1.5.

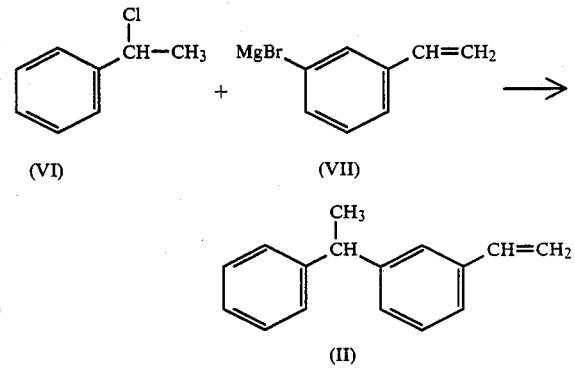

The catalyst and unreacted compounds are removed from the thus prepared reaction mixture containing 1-(3-vinylphenyl)-1-phenylethane and the compound is dehydrogenated in the presence of a dehydrogenation catalyst to obtain efficiently 1-(3-vinylphenyl)-1-phenylethylene of the formula (I).

As the dehydrogenation catalyst for this purpose, the conventional catalysts that are used, for example, in the dehydrogenation of ethylbenzene to produce styrene can be employed. For example, chromia-alumina catalyst and iron oxide catalyst can be exemplified. These catalysts can be used together with potassium carbonate or the oxide of chromium, cerium, molybdenum or vanadium as a promoter.

With regard to the pressure as a condition for the reaction, when the pressure is low, the reaction can proceed further. With regard to the temperature, the higher the temperature is, the further the reaction proceeds because it is an endothermic reaction. Accordingly, the reaction temperature is generally selected from the range of 500° to 700° C., and preferably 550° to 650° C. At a temperature below 500° C., the dehydrogenation reaction cannot proceed substantially. On the other hand, temperatures above 700° C. is not desirable because side reactions such as decomposition is caused to occur. The reaction pressure is from a reduced pressure to 5 kg/cm$^2$, and preferably from a reduced pressure to 3 kg/cm$^2$. In general, excess steam is used as a heating medium.

The contact time length in a continuous flow system is selected from the range of 0.01 to 10 hr$^{-1}$ as LHSV.

Through the above dehydrogenation reaction, the 1-(3-vinylphenyl)-1-phenylethylene can be efficiently prepared from the 1-(3-vinylphenyl)-1-phenylethane.

The carbonyl compound of the formula (III), α-(3-(1-phenylethenyl)phenyl)propionic acid or its alkyl ester can be prepared by subjecting the thus obtained the new compound, 1-(3-vinylphenyl)-1-phenylethylene, to the conventional carbonylation.

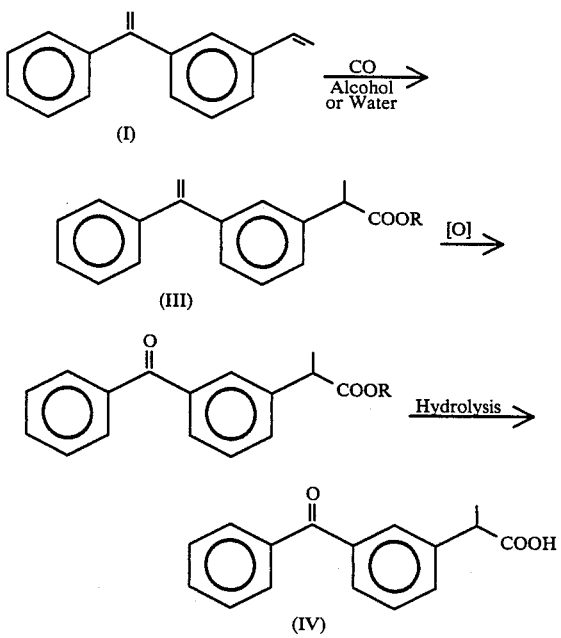

In the above formulae, R is a hydrogen atom or an alkyl group having 1 to 4 carbon atoms.

The catalysts used in the above carbonylation are exemplified by noble metal complex catalysts such as the complexes of Pd, Rh and Ir. Among them, the complex of Pd is especially preferable. These noble metal complexes have ligands of halogen atoms, trivalent phosphorus compounds, or carbonyl compound such as carbon monoxide. Usable noble metal, for example, palladium includes those of zero-valent or divalent.

The typical catalysts are exemplified by bistriphenylphosphine dichloropalladium, bistributylphosphine dichloropalladium, bistricyclohexylphosphine dichloropalladium, π-allyltriphenylphosphine dichloropalladium, triphenylphosphine piperidine dichloropalladium, bisbenzonitrile dichloropalladium, biscyclohexyloxime dichloropalladium, 1,5,9-cyclododecatriene dichloropalladium, bistriphenylphosphine dicarbonyl palladium, bistriphenylphosphine acetate palladium, bistriphenylphosphine dinitrate palladium, bistriphenylphosphine palladium sulfate, and tetrakistriphenylphosphine palladium.

In the use of the catalyst, it is added to the reaction system in the form of a complex. While, it is also possible to add a ligand separately so as to form a complex in the reaction system.

The use quantity of the catalyst is 0.0001 to 0.5 mole, preferably 0.001 to 0.1 mole to one mole of 1-(3-vinylphenyl)-1-phenylethylene. The addition quantity of the compound to form the ligand, is 0.8 to 10 moles, preferably 1 to 4 moles, to 1 mole of the noble metal of Pd, Rh or Ir.

The carbonylation is carried out at a temperature in the range of 40° to 150° C., preferably 70° to 120° C. The pressure of carbon monoxide is 20 to 700 kg/cm$^2$, preferably 40 to 500 kg/cm$^2$. In order to accelerate the reaction, an acid such as hydrogen chloride or boron trifluoride can be added.

The alcohols used in the carbonylation are lower alcohols having 1 to 4 carbon atoms such as methyl alcohol, ethyl alcohol, n-propyl alcohol, isopropyl alcohol, n-butyl alcohol, sec-butyl alcohol, tert-butyl alcohol, and isobutyl alcohol. Among them, methyl alcohol is preferable.

In the carbonylation, when 1-(3-vinylphenyl)-1-phenylethylene of the formula (I) is reacted in the presence of water, a carboxylic acid of the formula (III) in which R is a hydrogen atom can be obtained. When the reaction is carried out in the presence of a lower alcohol, an ester of the formula (III) is obtained in which R is the alkyl group of the lower alcohol. For example, when methyl alcohol is used, a methyl ester is prepared.

By oxidizing the carbonyl compound of the formula (III) prepared by the above process with a strong oxidizing agent, α-(3-benzoylphenyl)propionic acid of the formula (IV), ketoprofen, or its alkyl ester can be obtained. When an ester is oxidized, it can be converted in the form of an acid by the conventional hydrolysis operation before the oxidation. It is, of course, possible to oxidize the ester intact without the change of ester part. The strong oxidizing agents used for the oxidation are exemplified by permanganates and bichromates. The reaction is carried out by using one of or a mixture of solvents such as glacial acetic acid, acetic acid, isooctane, benzene and chloroform. The reaction temperature is in the range of 0° to 200° C., and preferably 30° to 150° C. By the above procedure, ketoprofen of the formula (IV) or its ester can be prepared.

The ester of ketoprofen having an R of an alkyl group can be converted into ketoprofen by the conventional hydrolysis without difficulty.

After the oxidation, the oxidizing agent is separated by filtration or the reaction mixture is subjected to extraction with an organic solvent such as benzene, ethyl acetate or chloroform. Then the resulting mixture is treated by distillation or re-crystallization to obtain a highly pure product of ketoprofen or its ester.

As described above in detail, it is possible to produce ketoprofen economically in a high yield and without difficulty by utilizing the new intermediate compounds of 1-(3-vinylphenyl)-1-phenylethylene and 1-(3-vinylphenyl)-1-phenylethane.

The present invention will be described with reference to examples which by no means limit the present invention.

Example 1

Synthesis of 1-(3-vinylphenyl)-1-phenylethylene (formula I)-(1)

To a 2 liter three-neck flask equipped with a dropping funnel, a reflux condenser and a stirrer was added 25.5 g (1.05 mole) of metallic magnesium and it was dried sufficiently by supplying dry nitrogen gas. After that, 50 ml of tetrahydrofuran which had been dried with a molecular sieve 5 A, was put into the flask and the contents were stirred vigorously. A solution of 183 g (1.0 mole) of 3-vinylbenzene bromide in 500 ml of dried tetrahydrofuran was dropped little by little over 2 hours. The reaction temperature was maintained at 75° to 80° C. and, after the addition of the solution, the stirring was continued for further 1 hour as it stands. Into the thus obtained Grignard reagent of 3-vinylphenylmagnesium bromide (formula VII), a solution of 122.6 g (1.02 mole) of acetophenone (formula VIII) in 500 ml of dried tetrahydrofuran was dropped little by little for 2 hours. The reaction temperature was maintained at 75° to 80° C. and, after the dropping, the stirring was continued for further 1 hour as it stands. The reaction mixture was then poured into 3 liter of an aqueous solution of 75 g of ammonium chloride and it was left to stand still for 20 hours and an oily layer was recovered to obtain 1-(3-vinylphenyl)-1-phenylethyl alcohol (VPA: formula V) in a yield of 89% (acetophenone basis) by distilling off the tetrahydrofuran.

To a 300 ml three-neck flask with a distillation column and a dropping funnel was added 81 g of potassium hydrogensulfate and the pressure was reduced to 15 to 20 mmHg. The obtained alcohol was then dropped into the flask little by little over 2 hours. The water and oily components produced by dehydration were recovered from the top of the distillation column and 1-(3-vinylphenyl)-1-phenylethylene was obtained in a yield of 100% (VPA basis) from the oily upper layer of a separatory funnel. The dehydration reaction was carried out at a temperature of 200° to 250° C.

The analytical data of the thus produced 1-(3-vinylphenyl)-1-phenylethylene (formula I) are shown in the following:

| Boiling Point: 134.0–135.5° C./2–3 mmHg | |
|---|---|
| IR: (Neat) cm$^{-1}$ | |
| 3050, 1690, 1495, 1260, 995, 900, | |
| 810, 780, 700 | |
| $^1$H—NMR: (CCl$_4$, δppm) | |
| 7.10–7.70 | (9H Multiplet) |
| 6.65–6.80 | (1H Quadruplet) |
| 5.65–5.80 | (1H Doublet) |
| 5.45–5.50 | (2H Doublet) |
| 5.20–5.30 | (1H Doublet) |
| Elemental Analysis: (as C$_{16}$H$_{14}$) | |
| Calculated: | C: 93.20% |
| | H: 6.80% |
| Found: | C: 93.24% |
| | H: 6.76% |

Example 2

Synthesis of 1-(3-vinylphenyl)-1-phenylethane (formula II)

To a 2 liter three-neck flask equipped with a 500 ml dropping funnel, a reflux condenser, and a stirrer was added 28 g (1.15 mole) of metallic magnesium and it was dried sufficiently by supplying dry nitrogen gas. After that, 50 ml of tetrahydrofuran which had been dried with a molecular sieve 5 A, was dropped into the flask and the contents were stirred vigorously. A solution of 183 g (1.0 mole) of 3-vinylbenzene bromide in 500 ml of dry tetrahydrofuran was dropped little by little over 2 hours. The temperature was maintained at about 80° C. and, after the dropping of the solution, the stirring was continued for further 1 hour as it stands. Thereby obtaining a Grignard reagent (3-vinylphenylmagnesium bromide: formula VII).

Then, 94 g (0.67 mole) of (1-chloroethyl)benzene of the formula (VI) and 5.4 g of the catalyst of nickel chloride (II) with ligands of 1,3-bis(diphenylphosphino)propane were mixed into 500 ml of dried ether. The above Grignard reagent was dropped little by little into this mixture over 2 hours. During the dropping, the temperature in the reactor was maintained at 0° C. After the dropping, stirring was continued for further 24 hours. The reaction mixture was then poured into iced water (1000 g of ice and 500 g of water) and aqueous layer and oily layer were separated to recover the oily layer. After that, ether and tetrahydrofuran were evaporated off under a reduced pressure to obtain 1-(3-vinylphenyl)-1-phenylethane in a yield of 74%.

The analytical data on the product are shown in the following:

| Boiling Point: 123.5–125.0° C./0.5–1.0 mmHg | |
|---|---|
| IR: (Neat) cm$^{-1}$ | |
| 2960, 1600, 1490, 1450, 990, | |
| 910, 790, 700 | |
| $^1$H—NMR: (CCl$_4$, δppm) | |
| 6.80–7.80 | (9H Multiplet) |
| 6.35–6.75 | (1H Quadruplet) |
| 5.45–5.75 | (1H Doublet) |
| 5.00–5.20 | (1H Doublet) |
| 3.85–4.35 | (1H Quadruplet) |
| 1.50–1.85 | (3H Doublet) |
| Elemental Analysis: (as C$_{16}$H$_{16}$) | |
| Calculated: | C: 92.31% |
| | H: 7.69% |
| Found: | C: 92.35% |
| | H: 7.65% |

Example 3

Synthesis of 1-(3-vinylphenyl)-1-phenylethylene (formula I)-(2)

A dehydrogenation catalyst (trademark: 64C made by Nissan Girdler Catalysts Co., Ltd., iron oxide catalyst with promoters of cerium and molybdenum) of 0.5 to 1 mm in particle diameter was fed into a fixed bed continuous flow reactor made of a stainless steel tube of 10 mm in inner diameter and 60 cm in length, thereby forming a catalyst bed of 20 cm in height. An oily substance containing 1-(3-ethylphenyl)-1-phenyletane which was obtained in the above Example 2 and pure water in a ratio of 1:5 were vaporized in the preheating tubes, and they were mixed together and fed to the catalyst bed to be dehydrogenated at a temperature of 550° C. and an SV of 0.25. Reaction product was cooled to room temperature and the vapor phase and liquid phase were separated to obtain an organic layer, which was subjected to reduced-pressure distillation at 2 to 3 mmHg to obtain a fraction of 134° to 136° C. As a result of GC analysis, it was understood that the fraction contained 59% by weight of 1-(3-vinylphenyl)-1-phenylethylene and 41% by weight of other hydrocarbons.

The thus obtained 1-(3-vinylphenyl)-1-phenylethylene (formula I) was then refined and analyzed. The results of analysis were the same as those in Example 1.

Example 4

Synthesis of 1-(3-vinylphenyl)-1-phenylethylene (formula I)-(3)

By using a dehydrogenation catalyst (trademark: G64A made by Nissan Girdler Catalysts Co., Ltd., iron oxide catalyst with promoters of potassium carbonate and chromium oxide), an oily substance containing 57.4% by weight of 1-(3-vinylphenyl)-1-phenylethylene and 42.6% by weight of other hydrocarbons was obtained from the above oily substance containing 1-(3-ethylphenyl)-1-phenylethane at a reaction temperature of 500° C., LHSV of 1.0 and a molar ratio of $H_2O$/starting material of 3.0.

Example 5

Synthesis of α-(3-(1-phenylethenyl)phenyl)propionic acid (formula III)

To a 500 ml autoclave with a stirrer were added 43 g of 1-(3-vinylphenyl)-1-phenylethylene obtained in Example 1, 5.5 g of bistriphenylphosphine dichloropalladium, 80 g of 10% aqueous solution of hydrochloric acid and 80 ml of toluene as a solvent. After the pressure was raised up to 100 kg/cm$^2$ by carbon monoxide at room temperature, with raising the temperature to 120° C., the pressure was raised to 300 kg/cm$^2$. After the absorption of carbon monoxide by the reaction was ceased, the reaction was still continued for 24 hours.

After the reaction, the autoclave was cooled and reaction mixture was recovered. The oily layer and aqueous layer were separated by a separatory funnel. The oily layer was extracted three times with 50 ml of 8% aqueous solution of sodium hydroxide. The aqueous extraction solution were combined with the above separated aqueous layer and the pH was adjusted to 2 by adding hydrochloric acid. After that extraction was done three times with 500 ml of chloroform. The chloroform was removed from the extract liquid by reduced pressure evaporation to obtain 44.7 g of pale yellow crystals of α-(3-(1-phenylethenyl)phenyl)propionic acid.

The analytical results of the product are shown in the following.

| | |
|---|---|
| Melting Point: 69.0–71.0° C. | |
| IR: (Neat) cm$^{-1}$ | |
| 3030, 2750, 2650, 1715, 1610, 1420, | |
| 1240, 1070, 910, 785, 710 | |
| $^1$H—NMR: (CCl$_4$, δppm) | |
| 12.2 | (1H Singlet) |
| 6.80–7.50 | (9H Multiplet) |
| 5.38 | (2H Singlet) |
| 3.45–3.90 | (1H Quadruplet) |
| 1.35–1.65 | (3H Doublet) |
| Elemental Analysis: (as C$_{17}$H$_{16}$O$_2$) | |
| Calculated: | C: 80.95% |
| | H: 6.35% |
| | O: 12.70% |
| Found: | C: 80.91% |
| | H: 6.32% |
| | O: 12.77% |

Example 6

Synthesis of α-(3-benzoylphenyl)propionic acid (ketoprofen)-(1)

α-(3-(1-Phenylethenyl)phenyl)propionic acid (35 g) obtained in Example 5 was dissolved in 250 ml of benzene and 250 ml of water was further added thereto with vigorous stirring to prepare a suspension. Then, 2 liter of 2% aqueous solution of potassium permanganate was dropped little by little over 1.5 hours. After the dropping, stirring was continued for 18 hours at room temperature. After the reaction, it was acidified by adding concentrated sulfuric acid and was treated by adding 35 g of sodium sulfite. After that, 500 ml of water was added and extraction was carried out three times with 150 ml of ether. The ether solution was washed with water and it was extracted three times with 200 ml of 5% aqueous solution of sodium hydroxide. It was then acidified by adding hydrochloric acid and extracted again three times with 150 ml of ether, which was followed by washing with water, drying with anhydrous magnesium sulfate, and filtration. The ether was then removed by reduced-pressure evaporation. Finally, 20 g of α-(3-benzoylphenyl)propionic acid (ketoprofen) was obtained by re-crystallization from benzene/petroleum ether mixture. The melting point and spectrum were the same as those of an authentic sample.

Example 7

Synthesis of α-(3-(1-phenylethenyl)phenyl)propionic acid methyl ester (formula III)

To a 500 ml autoclave with a stirrer were added 43 g of 1-(3-vinylphenyl)-1-phenylethylene obtained in Example 1, 0.74 g of palladium chloride (II), 2.19 g of triphenylphosphine, 13.4 g of methyl alcohol and 90 ml of toluene as a solvent. The pressure was raised up to 150 kg/cm$^2$ by carbon monoxide at room temperature. Further, the temperature was raised to 125° C. and the pressure was raised simultaneously to 400 kg/cm$^2$. After the absorption of carbon monoxide by the reaction was ceased, the reaction was still continued for 16 hours. After the reaction, the reaction mixture was subjected to reduced-pressure distillation to obtain α-(3-(1-phenylethenyl)phenyl)propionic acid methyl ester having a boiling point of 144.5° to 145.5° C. at 2 to 3 mmHg was obtained in a yield of 87%. The data of spectrum analysis are shown.

| | |
|---|---|
| IR: (Neat) cm$^{-1}$ | |
| 3040, 2995, 2960, 2880, 2850, 1740, | |
| 1610, 1500, 1445, 1340, 1260, 1190, | |
| 1075, 1032, 905, 785, 710 | |
| $^1$H—NMR: (CCl$_4$, δppm) | |
| 6.70–7.30 | (9H Multiplet) |
| 5.32 | (2H Singlet) |
| 3.20–3.75 | (4H Multiplet) |
| 1.45–1.56 | (3H Doublet) |
| Elemental Analysis: (as C$_{18}$H$_{18}$O$_2$) | |
| Calculated: | C: 81.20% |
| | H: 6.77% |
| | O: 12.03% |
| Found: | C: 81.20% |
| | H: 6.80% |
| | O: 12.00% |

Example 8

Synthesis of α-(3-benzoylphenyl)propionic acid (ketoprofen)-(2)

α-(3-(1-Phenylethenyl)propionic acid methyl ester (36 g) obtained in Example 7 was dissolved in 250 ml of benzene and 250 ml of water was further added thereto with vigorous stirring to prepare a suspension. Then, 2 liter of 2% aqueous solution of potassium permanganate was dropped little by little over 1.5 hours. After the dropping, stirring was continued for 18 hours at room temperature. After the reaction, the reaction mixture was acidified by adding concentrated sulfuric acid and was treated by adding 35 g of sodium sulfite. After that, 500 ml of water was added and extraction was carried out three times with 150 ml of ether. The ether solution was washed with water. The remaining layer was hydrolyzed with 5% aqueous solution of sodium hydroxide at the refluxing temperature for 5 hours. After cooling, the aqueous layer was washed with ether. The aqueous layer was acidified by adding hydrochloric acid and extracted again with ether, which was followed by washing with water, drying with anhydrous magnesium sulfate, and filtration. Ether was then removed by reduced-pressure evaporation to obtain crude product. Finally, 23 g of α-(3-benzoylphenyl)propionic acid (ketoprofen) was obtained by re-crystallization from benzene/petroleum ether mixture. The melting point and spectrum were the same as those of an authentic sample.

What is claimed is:

1. A compound of the following formula:

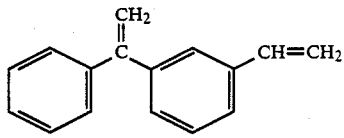

(I)

2. A compound of the following formula:

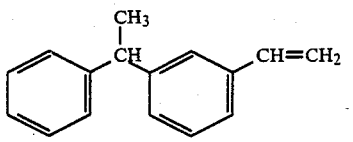

(II)

* * * * *